(12) United States Patent
Perrault et al.

(10) Patent No.: US 7,252,792 B2
(45) Date of Patent: Aug. 7, 2007

(54) MEDICAL ELECTRODE

(75) Inventors: James J. Perrault, Vista, CA (US); Solomon E. Shenkute, San Diego, CA (US); Steve Heard, Escondido, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 565 days.

(21) Appl. No.: 10/896,303

(22) Filed: Jul. 21, 2004

(65) Prior Publication Data

US 2005/0085706 A1 Apr. 21, 2005

Related U.S. Application Data

(62) Division of application No. 10/256,653, filed on Sep. 27, 2002, now Pat. No. 6,842,636.

(51) Int. Cl.
*H01B 1/00* (2006.01)
*B32B 7/12* (2006.01)
*C08F 2/50* (2006.01)

(52) U.S. Cl. ............ 252/500; 252/510; 252/511; 428/355 R; 428/355 AC; 600/391; 600/392; 522/40

(58) Field of Classification Search ........ 255/500, 255/510, 511; 428/355 R, 355 AC, 500, 428/523; 522/40, 181; 600/391, 392, 397
See application file for complete search history.

(56) References Cited

U.S. PATENT DOCUMENTS

| | | | | |
|---|---|---|---|---|
| 4,352,359 A | * | 10/1982 | Larimore et al. | 600/395 |
| 4,543,371 A | * | 9/1985 | Gallop et al. | 523/106 |
| 4,810,418 A | * | 3/1989 | Burvee | 252/500 |
| 5,352,713 A | * | 10/1994 | Snyder et al. | 522/40 |
| 5,393,798 A | * | 2/1995 | Weber | 521/149 |
| 5,645,062 A | * | 7/1997 | Anderson et al. | 600/391 |
| 5,712,356 A | * | 1/1998 | Bothe et al. | 526/264 |
| 5,763,554 A | * | 6/1998 | Prosise et al. | 526/271 |
| 5,936,052 A | * | 8/1999 | Bothe et al. | 526/264 |
| 2003/0120231 A1 | * | 6/2003 | Wang et al. | 604/368 |

OTHER PUBLICATIONS

R.Schwalm et al, "Vinyl.Ethers in UV Curing: Copolymers with Acrylates and Unsaturated Polyesters" BASF AG, D-67056, pp. 103-109, Ludwigshafen, Germany. No Date.*
Christian Decker, "Recent Developments in Radiation Curing Chemistry," Radtech Report, Nov./Dec. 1993, pp. 14-21.*
C. Decker and D. Decker, "Kinetic and Mechanistic Study of the UV-Curing of Vinyl Ether based Systems RadTerch '94 North America UV/EB Conference and Exhibition Proceedings," Orlando, Florida, May 1-5, 1994, pp. 602-616.*
Masatoshi Miyamoto, "Radical Polymerization of Oligoethylene GlycolMethyl Vinyl Ethers in Protic Polar Solvents," macromol. Chem. Phys., 1998, vol. 199, pp. 119-125.*

* cited by examiner

*Primary Examiner*—Mark Kopec
*Assistant Examiner*—Kallambella Vijayakumar
(74) *Attorney, Agent, or Firm*—Walter A. Hackler

(57) ABSTRACT

An electrode providing electrical contact with a patient's skin includes a conductive member adapted for connection to an external electrical apparatus and a non-liquid water containing film for electrically interfacing to said patient's skin, the non-liquid film being electrically and mechanically connected to said conductive member. The non-liquid water containing film includes an electrically conductive organic polymer plasticized with a polyhydric alcohol with said organic polymer being derived from a monomeric mixture comprising from about 2 to 30 pph acrylic acid, 2 to 30 pph of a glycolvinylether and 0.01 to 1.5 pph of a crosslinking agent. Preferably the polyhydric alcohol is glycerol.

16 Claims, 2 Drawing Sheets

MEDICAL ELECTRODE

The present application is a division of U.S. application Ser. No. 10/256,653 filed Sep. 27, 2002, now U.S. Pat. No. 6,842,636.

FIELD OF THE INVENTION

The present invention provides a combination electrode for use in medical applications, e.g., medical applications requiring monitoring and stimulation and return of current, having an electrical current conductor including a connector in addition to a skin-interfacing film wherein this film may have adhesive, plastic and hydrophilic properties such as may reside in an electrically conductive, polymeric composition.

BACKGROUND OF THE ART

Medical electrodes have, in the past, taken many shapes and forms. Principally, they have been shaped according to the use for which they are intended. Electrodes used with monitoring apparatus, such as EKG and EEG machines, commonly have small round contact surfaces, whereas electrodes used with such stimulation apparatus as pain control devices tend to be larger and have rectangularly and other conveniently shaped contact surfaces. Whether intended for monitoring or stimulation use, a design objective for each electrode group has been, and continues to be, good electrical signal transmission between a patient's skin surface and the electrical cables connected to a particular piece of apparatus. With respect to stimulation and monitoring electrodes, efficient signal transmission across the epidermis conductor interface is desirable. Further, with respect to stimulation electrodes, effective signal transmission free of current concentration points or "hot spots" is also desirable.

Of the electrodes presently available, many offer combination structures including a metallic or otherwise conductive support member to which an electrical wire from an associated apparatus may be attached.

Certain of the currently available electrodes, including electrical stimulation electrodes are disclosed in U.S. Pat. Nos. 4,722,354; 4,736,752; 4,819,328; 5,038,796 and 5,450,845 to Axelgaard et al which are hereby incorporated by-reference to show various electrode designs including but not limited to medical electrode shapes, structures, materials and methods for connecting said medical electrodes to the appropriate electrical apparatus.

In many instances, the medical electrodes of the prior art need the addition of generous amounts of an electrode paste or gel applied directly to the conductive support member to enhance conductivity across the skin-electrode interface to the point where acceptable operating conditions are achieved.

Other prior art electrodes teach the incorporation of an open cellular skin interface pad secured to a conductive support member. This pad, as shown in U.S. Pat. No. 3,817,252, is often sponge material which functions to hold an amount of electrolyte solution in order to enhance conductivity across the skin-pad interface. Such an interface pad can be, alternately, saturated with electrode pastes or gels of the type that do not run or evaporate as readily as electrolyte solutions.

The prior art electrodes that require an electrode paste or gel or electrolyte solution provide a structure which does not always maintain constant, efficient and effective electrical transmission for long periods of time without the need for additional electrode paste, gel or solution. Moreover, there is a tendency while using these electrodes, for the electrode gel to separate and/or to flow to a nonuniform thickness. Under these conditions, sections of the conductive support member could be exposed to the skin and local hot spots can result which can cause discomfort if not severe enough to cause burns to the patient's skin. Therefore, medical electrodes wherein the adhesive, itself, provides the conductive interface between the skin and the electrical connector are very desirable. An electrode of this type is disclosed in U.S. Pat. No. 4,066,078 to Berg. In this patent, the polymer itself acts as the adhesive and, through the quaternary groups attached to the polymer backbone, provides a conductive interface.

Nevertheless, others have continued to formulate adhesive materials that effectively adhere to the skin and the materials that can be utilized in fabricating a medical electrode and also provide adequate conductivity. See, for example, U.S. Pat. Nos. 4,830,776; 4,274,420; 4,777,954; 4,699,146; 4,458,696; 5,024,227; 4,243,051; 6,115,625, etc., which exemplify the continuing search for conductive adhesive materials for use in medical electrodes.

Acrylic hydrogels are commonly used biomedical hydrogels due to low cost, absorbency, and ease of fabrication. These hydrogels may be used as contact lens materials as disclosed in U.S. Pat. No. 5,712,356 and as conductive electrode adhesives as disclosed in U.S. Pat. No. 5,868,136.

Vinyl ether monomers are biocompatible and environmentally friendly, and glycol vinyl ether monomers are water-soluble. Vinyl ether homopolymers are also flexible and elastic. The only commercial method of vinyl ether homopolymerization is cationic and can not be done in the presence of water.

It has now been found that the free radical copolymerization of glycol vinyl ether monomers with acrylic monomers in water promotes a high degree of acrylic polymerization and imparts greater flexibility and elasticity to the resulting acrylic copolymer than other co-monomers. Moreover, as compared to acrylic hydrogels without copolymerized glycol vinyl ether, copolymers of acrylic acid and a glycol vinyl ether provide films that are softer, has less aggressive adherence to skin and separate from skin without stringing or leaving residue on the skin.

However, a major problem that had to be overcome was that water-soluble acrylic monomers hydrolyze glycol vinyl ether monomers at the optimum conditions for free radical polymerization. A by-product of this hydrolysis is an irritating aldehyde. This problem has been solved by the present invention by reacting these aldehydes into biologically benign compounds. The amount of irritating residual acrylic monomers is also reduced by the high degree-of-polymerization of the electrode adhesives of this invention.

An objective of this invention, therefore, is to provide an electrode with an improved electroconductive skin-interface substrate, which will perform a similar function to, and eliminate the need for, an electrolyte solution, electrode paste or electrode gel.

Another objective of this invention is to provide an electrode with a skin-interface substrate having pressure sensitive adhesive properties which will enable the electrode to adhere to the skin without the use of tape or other securing mediums.

Another objective of this invention is to provide an adhesive substrate that has high tack so that minimal pressure is needed to apply it to the skin but is such that it can also be easily separable from the skin upon removal without any noticeable residue.

A further objective is to provide an electrode with a non-liquid skin-interface which is a film which will maintain a uniform thickness and will not separate to expose sections of a conductive support member to the skin.

Yet another object is to provide an electrode with an electroconductive skin-interface that will not dry out or decomposed for period of years even if exposed to the atmosphere.

An even further objective is to provide an electrode having a skin-interface substrate which will not decompose or dry out like electrodes utilizing electrolyte solutions under long periods of use.

Other objects and advantages of the present invention will become apparent from a careful reading of the specification below.

SUMMARY OF THE INVENTION

The objectives of this invention are accomplished in a medical electrode, suitable for stimulation, monitoring applications and return of current, including an electrically conductive member capable of being connected to an external electro-medical apparatus. This conductive member may be a pliable sheet of material preferably having connected thereto a medium for securing positive electrical connection between the conductive member and the external electro-medical apparatus. Attached to the underside of the conductive member and extending away from the electrical connection is, an electrically conductive skin-interface substrate material, preferable in the form of a film. This material must have adhesive properties so that it will adhere to the skin of a patient. Preferably, this material also has plastic and hydrophilic properties. A suitable combination of the aforementioned adhesive, plastic and hydrophilic properties is provided by an adhesive composition which comprises an electrical conductive organic polymer plasticized with a polyhydric alcohol, e.g., glycerol.

Suitable electrically conductive organic polymers useful in the adhesive composition utilized in the medical electrode of the present invention include copolymers derived from the polymerization of acrylic acid and a glycol vinylether. Such copolymer may further include the following comonomers: 2-acrylamido propane sulfonic acid, methylenebisacrylamide and acryloxyethyl dimethyl ammonium chloride and other cationic acrylic esters.

The adhesive composition may also include an aldehyde reactant such as, but not limited to, hydrogen peroxide, 2-hydroxyethylethylene urea (HEU) or L-arginine hydrochloride.

The precursor to said adhesive composition is copolymerized to yield a film having suitable adhesive properties and electroconductivity properties for use as a medical electrode adhesive in the presence of an ultraviolet sensitive curing agent such as 2-hydroxy-2-methyl-1-phenyl-propan-2-one (available as Darocure 1173®),4-2-hydroxyethoxy)-phenyl-(2-hydroxy-2-phenyl-(2-hydroxy-2-propyl)ketone (available as Darocure 2959®), or 2,2-dimethoxy-2-phenylacetophenone (available as Irgacure® 651)1-[4-(2-Hydroxyethoxy)-phenyl]-2-hydroxy-2-methyl-1-propane-1-one (as available as Irgacure® 2959) and trimethyl benzoyldiphenylphosphine oxide (available as Esacure DP250) or 1-hydroxycyclohexylphenyl ketone (available as Irgacure 184.) (Other initiators are disclosed in U.S. Pat. Nos. 5,800,685, 6,115,625 cited above). These patents are incorporated herewith in their entirety by this specific reference thereto.

BRIEF DESCRIPTION OF THE DRAWINGS

The invention will be more readily understood by reference to the drawings wherein like numerals refer to like elements and in which.

DETAILED DESCRIPTION OF THE INVENTION

Medical electrodes are intended for usage as efficient and effective transmission mediums between a patient's skin and an electro-medical apparatus. Primary to their operation is a uniform conductivity through the electrode itself and a uniform conductivity across the electrode skin-interface. Uniform conductivity through an electrode is most often interrupted by a non-uniformity in the electrode materials. Uniform conductivity across the electrode skin-interface is most often interrupted by a separation-of some or all of the electrode interfacing material in contact with a patient's skin.

Preferably, the electrode is intended to be disposable. It is also intended to have adhesive properties sufficient to be self-adhering to a patient's skin for weeks without drying out. In fact, the adhesive properties of the gel in accordance with the present invention have been maintained for more than 3 years, without drying out. However, the gel has sufficient flexibility and elasticity to move as a patient's skin moves while returning to original shape when permitted. Additionally, it is intended to provide uniform conductivity with even current densities of approximately 30 microamperes per square millimeter when subjected to a stimulus of about 60 milliamperes at 35 cycles per second having a pulse duration of about 250 microseconds. This electrode is intended to be easily handled, non-irritating to a patient's skin, and sterilizable.

Figure 1:
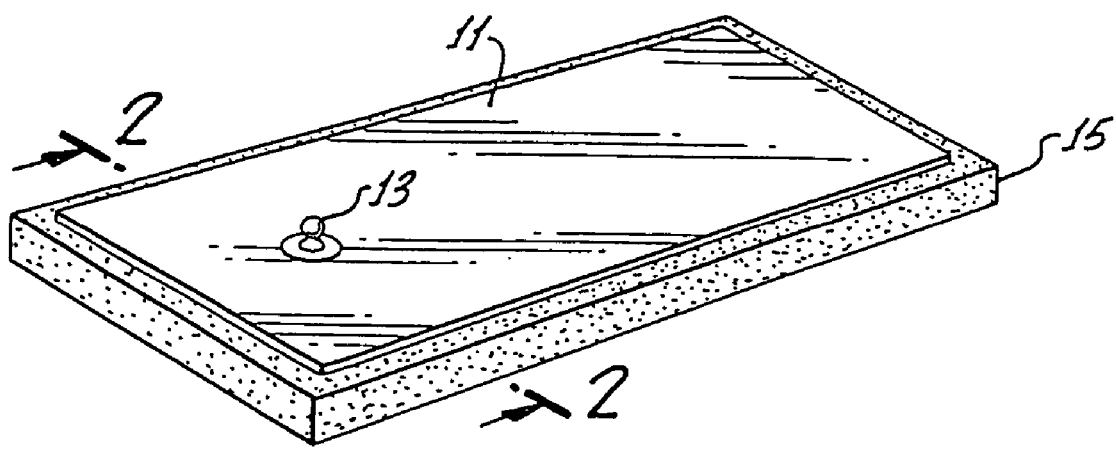
FIG. 1 shows a perspective view of the electrode.

The electrode configuration is shown in FIG. 1. A conductive member 11 is cut, stamped or otherwise shaped out of a piece of conductive material which may be aluminum foil or a polyester, e.g., a polyethylene terephtalate (Mylar®) coated with aluminum or tin. The shape to which this conductive member 11 is formed will depend upon the particular application in which it is to be used. The shape is sometimes round but may be as shown in FIG. 1, rectangularly shaped.

Alternately, other metallic foils, conductive polymers, graphitized or metalized cloth or wire mesh may be used as the conductive member. In particular, the knit conductive fabric disclosed in U.S. Pat. No. 4,722,354 may be utilized as the conductive member. For each material, an appropriate strength and thickness is to be chosen to yield a pliable, yet sufficiently strong member 11. When the conductive member 11 is of aluminum foil, it usually is of 1-10 mil thickness.

Secured to the outer surface of the conductive member 11 is a connector 13 for providing a medium to which external signal cables may be attached for electrically communicating with the conductive member 11. This connector 13 may be a conductive swaged snap fastener 13, as shown in the accompanying drawings, which is available commercially. This fastener 13 is mechanically and electrically attached to the conductive member 11, extending perpendicularly from the outer surface of this member 11. Alternatively, when the conductive member is a knit conductive fabric, the electrical connector may be stranded stainless steel as shown in U.S. Pat. No. 4,722,359.

Abutting the inner surface of the conductive member 11 is an electrically conductive skin-interface substrate 15. This substrate 15 is a layer of material being typically a film or sheet which will be described below.

The conductive substrate 15 is shaped correspondingly to the conductive member 11. When constructed in combination with a rectangular member 11, the substrate 15 is also rectangular. The film thickness of this substrate 15 is uniform throughout, however, this uniform film may be of various thicknesses. A range of 10 to 100 mils, e.g., about 50 mils is common.

As will be discussed below, the substrate 15 is a film or sheet having adhesive properties, thus when it is brought into contact with the conductive member 11, it will adhere to that member 11 providing electrical connection with it.

Figure 2:
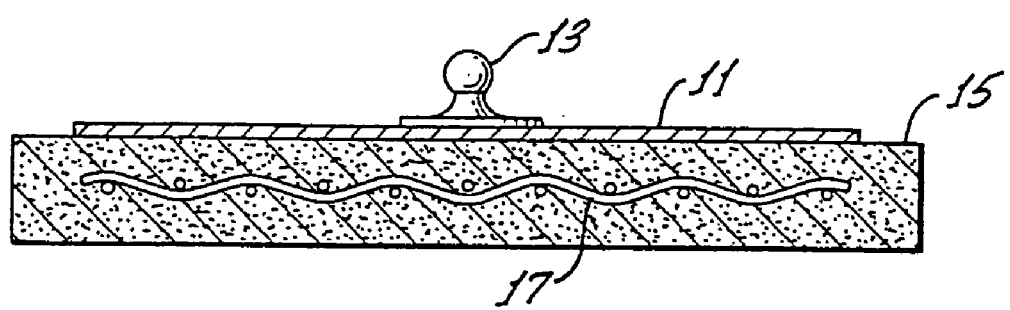
FIG. 2 shows a cross-section in side elevation through the electrode of FIG. 1.

A supporting scrim 17, FIG. 2 may be used in electrode configurations where a greater thickness substrate 15 film is used. This scrim 17, while not a necessary part of the electrode, will tend to support by being distributed throughout the substrate 15. A further advantage to the use of this scrim 17 is that it acts to reinforce and strengthen the substrate 15.

The scrim 17 is positioned within and through the thickness of the substrate 15, in alignment with the conductive member 11, and is of a size to extend completely under the conductive member 11. The scrim 17 can be a woven or non-woven spun-bonded polyester fabric, a net of a stretched, embossed melt-extruded polymeric film, a sheet of polyolefin monofilaments heat-sealed together at their interstices, a thin sheet of a thermoplastic polymer with holes heat-stamped in a geometric pattern or any other supportive media. The scrim 17 may be any material allowing transmission of light for curing if only cured from one side. Also, the scrim 17 should retain most of its strength when wetted by the monomeric mixture.

In operation, the electrode is applied with the substrate 15 in direct contact with the skin. The adhesive properties of the substrate 15 eliminate the necessity for tape or other securing mediums to hold the electrode in continuous contact with the skin. The swaged fastener 13, or other suitable connector, receives electrical signals from an external apparatus. These signals are conducted into the conductive member 11 which in turn directly conducts them into the substrate 15. In this manner, current densities are uniformly distributed over the area of the substrate 15 in contact with the conductive member 11 and, in turn, are uniformly transmitted to the skin surface in contact with the substrate 15.

Primary to the unique structure of the electrode for eliminating the need for added electrode pastes, gels or electrolyte solutions, and for eliminating the need for securing mediums to hold the electrode in place, are the composition and structure of the substrate 15 material, enabling it to possess the desired physical, chemical and electrical properties.

Substrate 15 is a sheet or film of an electrically conductive organic polymer plasticized with a polyhydric alcohol, preferably glycerol.

The electrically conductive organic polymers that are utilized in preparing substrate 15 are derived from the copolymerization of a mixture of monomeric acrylic acid and a glycolvinylether. Said organic polymer may comprise 10 to 75 parts per hundred, by weight (pph), e.g., 30 to 60 pph, acrylic acid and 75 to 25 pph, e.g. 70 to 40 pph, of a glycolvinylether. In addition, the above mixture of comonomers, the organic polymer, may further include additional comonomers; in particular, the acrylic acid may be completely or partially replaced with AMPS.

Preferably the glycolvinylether may be selected from the group consisting of hydroxybutyl vinyl ether ethyleneglycolvinylether, diethyleneglycolmonovinylether, and triethyleneglycolmethylvinylether. Most preferably the glycolvinyl ether is diethylene glycol monovinyl ether.

Furthermore, the organic polymer may comprise about 0.01 to 1.5 pph of a crosslinking agent, such as methylene bisacrylamide, to increase the molecular weight and cohesivity of the conductive organic polymer through crosslinking. Other comonomers having at least two copolymerizable olefinic moeities, especially difunctional or trifunctional derivatives of acrylic acids, may be utilized. For example, polyethylene glycol dimethacrylates and diacrylates having a molecular weight of from about 200 to about 600 and ethoxylated trimetholpropane triacrylate (ETMPTA) are preferred crosslinking agents.

The comonomer mixture that is copolymerized to provide the conductive organic polymer will also include a polyhydric alcohol, e.g., polyhydroxyhydrocarbons and oxyalkyls, e.g., polyetheneglycol, sorbitol, glycerol, etc. to plasticize the organic polymer. The polyhydric functions as a humectant, i.e., it absorbs moisture and promotes conductivity of the substrate 15. The polyhydric alcohol may comprise from 25 to 75 pph, preferably from 40 to 60 pph, e.g., about 37 to 53 pph of the comonomer mixture. Most preferably, the polyhydric alcohol is glycerol.

The comonomer mixture that is copolymerized to provide the conductive organic polymer may also include a thickening agent. The thickening agent may be a high molecular weight polymer or copolymer such as a N-vinylpyrrolidone/vinylacetate copolymer (Luviskol VA 73W or VA 64W) available from BASF; methylvinylether/maleic anhybrid copolymer (Gantrez® S95), which is available from ISP; ethylene/maleic anhydride (EMA) Copolymer, which is available from Zeeland Chemical; and N-vinylpyrrolidone/acrylic acid Acrylidone® (ACP-1041 or Acrylidone 1005), which is available from ISP, and may comprise from about 0.5 to 8 pph of the comonomer mixture, e.g., about 2 to 5 pph. The N-vinyl pyrrolidone/vinylacetate copolymer disclosed above is especially preferred for use in the compositions of this invention.

Magnesium acetate may also be included when the electrode is utilized as a stimulating electrode. Potassium chloride may be added when the electrode is utilized as a sensing electrode.

The above comonomer mixture is preferably copolymerized or cured by thermal or ultraviolet (UV) radiation. Therefore, an ultraviolet sensitive curing agent is provided in the comonomer mixture at a concentration of from 0.05 to 3 pph, preferably from 0.5 to 2.0 pph. Suitable curing agents are 2-hydroxy-2 methyl-1-phenyl-propan-2-one (available as Darocur 11730®), 4-(2-hydroxyethoxy)phenyl (2-hydroxy-2-phenyl (2-hydroxy-2-propyl)ketone (available as Darocure 2959™), 2,2-dimethoxy-2-phenyl acetophenone (available as Irgacure® 651), 1-[4-(2-Hydroxyethoxy)-phenyl]-2-hydroxy-2-methyl-1-propane-1-one (available as Irgacure® 2959) or 1-hydroxycyclohexylphenylketone (available as Irgacure 184), all of which are available from Ciba-Geigy and trimethyl benzoyl diphenyl phosphine oxide (available as Esacure DP250).

Thus, to prepare the substrate 15, the following gelled comonomer mixtures may be subjected to thermal or ultraviolet polymerization conditions:

| Ingredient | Broad Range pph | Preferred Range pph |
| --- | --- | --- |
| acrylic acid | 2-20 | 4-12 |
| glycolvinylether | 2-20 | 3-10 |
| crosslinker | 0.01-3 | 0.01-2.0 |
| thickener | 0-8 | 0-3.0 |
| glycerin | 25-75 | 35-60 |
| UV sensitive curing agents | 0.5-3 | 0.5-1.5 |
| distilled water | 10-40 | 15-30 |

The acrylic acid is preferably partially neutralized with a basic potassium or sodium oxide, hydroxide, or carbonate or amine, e.g. triethanolamine. For example, from 25 to 75 molar percent acrylic acid may be neutralized.

A buffer may also be included in the comonomer mixture, e.g. from 0.2 to 2 pph of potassium sodium tartrate, or aluminium potassium sulfate (a further function of the $AL^{+3}$ ion of the above buffer and $Mg^{+2}$ ions, as well, is that such ions function as firming agents for the compositions of this invention).

Finally, an aldehyde reactant or neutralization agent may be included to remove any aldehyde generated by the acid hydrolysis of the vinyl ether monomer. Suitable aldehyde reactants include hydrogen peroxide, e.g. from about 1 to 3 pph; 2-hydroxyethylethylene urea, e.g. from about 1 to 5 pph; and L-arginine hydrochloride, e.g. from about 1 to 5 pph. Most preferably the aldehyde reactant is 2-hydroxyethylethylene urea at from 3 to 5 pph.

The above conductive substrate has a capacity for absorbing and retaining large amounts of water. This property further promotes the conductivity of the copolymer.

As previously mentioned, while the above disclosed substrate will absorb large amounts of water, it is substantially insoluble in water because the conductive organic polymer contains at least 0.02 parts by weight per 100 parts of monomer of a crosslinking agent.

The substrate 15 compositions exhibit a tackiness which can be increased as the glycerol concentration is increased. As water and/or salt water is absorbed, the surface of the substrate material 15 softens. As a result, the substrate 15 will flow into pores and other irregularities in the skin, creating a mechanical interlock bond with the skin in addition to the already present adhesive bond. The bonding and, concomitantly, the electrical transmission of the electrode are enhanced as it "ages" in contact with the skin.

Importantly, the flexibility and elasticity of the substrate imparted by the glycol vinyl ether co-monomer make it appear that the substrate 15 never dries out. Actually, the water content does go up and down with the ambient humidity but it is not apparent to the user because the physical properties remain relatively unchanged. Enough water is retained that the electrode remains electrically functional even in dry conditions for months or years as hereinafter reported.

The UV free radical polymerization reaction of acrylic acid and glycol vinyl ether is so strongly driven that relatively large amounts of glycerol can be incorporated compared to other UV cure hydrogels. [Also the acrylic acid can be completely reacted in the presence of glycerol if the proper amounts of glycol vinyl ether and UV initiator are used.] This is to be compared with prior art substrates which typically contain about 20%-40% water and little or no glycerol causing drying to occur within hours.

The flow condition eliminates air spaces between the skin and the substrate 15 to greatly reduce the impedance across the interface. This in turn greatly reduces the heat normally created at this interface. While the surface portion of the substrate 15 will flow, the greater portion of its mass will remain intact. Thus, the material resists separation or the development of irregular thicknesses. As a result, two heat and/or burn producing conditions, i.e., a high resistance across the interface due to an air layer which creates high temperatures over the entire interface, and the physical contact of the conductive member 11 directly to the skin creating a shunt of the current to a small area and generating extreme temperature in that area, are avoided.

A secondary electrical effect is also improved as the electrode "ages." Present during the operation of all electrodes is a battery effect created at the skin interface due to the capacitance across this interface. This battery effect causes some current to tend to circle backward towards its source of flow creating eddy currents. With this electrode of the invention, as water and body salts are absorbed into the electrode substrate, the interface area becomes more ionically (i.e., electrically) homogenous, thus reducing the battery effect and any resulting eddy currents.

The electrode may be packaged for use in a sealed or unsealed envelope of any of a number of suitable materials such as polyethylene or other plastic film. Foil barrier packaging, as used with prior art electrodes, is not required for the present invention. Packaging of the present invention is only required for product identification and to prevent contamination. In that regard, a release paper or film of a waxed or plastic-coated type can be used to protect the substrate 15 before application to a skin surface.

The invention is further illustrated by the following examples which are illustrative of a specific mode of practicing the invention and is not intended as limiting the scope of the appended claims.

EXAMPLE I

Acrylic acid and glycol vinyl ethers copolymerize via a charge transfer complex wherein the vinyl ether acts as an electron donor and the acrylic acid acts as an electron acceptor. This reaction occurs in a matter of minutes if just these two materials are mixed together generating very low molecular weight species; however, high molecular weight species (>10,000) can be created with a free radical initiator. Molecular weights should be greater than about 100,000 daltons to be adhesive and leggy and less than about 5,000,000 daltons, as a higher molecular weight may be too firm at the level of crosslinking preferred. Mixing and curing of the ingredients, utilized in the below examples, must be done quickly to avoid the generation of a significant concentration of aldehydes from the acid hydrolysis of the vinyl ether by the acrylic acid and to avoid generation of low molecular species by autopolymerization.

The following formulation is utilized as a conductive substrate. This formulation is prepared as follows: Into a stainless steel mixing container, equipped with a mechanical stirrer, is added 62.4 g of deionized water. With slow agitation, 3 g of sodium hydroxide and 6 g of potassium chloride are slowly added to the water. After allowing the stirred caustic solution to cool to room temperature, 48 g acrylic acid, 24 g of diethyleneglycolmonovinylether, 150 g of glycerin and 2.7 g of a 1% solution of methylenebisacrylamide, in that order, are slowly added to the water containing solution. The resulting mixture is stirred for an additional 15 minutes while the solution is purged with a slow stream of nitrogen gas to displace the residual dissolved oxygen gas from the solution. Finally, a mixture of 0.9 g of CN 383 and 3 g of Irgacure® 184 is poured into the stirred water containing solution. The resulting mixture is coated on and penetrates a polyester scrim, such as Reemay® 1006 or 2250 to provide a coating thickness of between 10 to 100, e.g., about 40 to 60 mils. Typical line speeds for the coating process vary from 10 to 100, e.g., 30 to 60 linear feet per minute. The coated polyester scrim is irradiated with ultraviolet radiation from a UV source, such as the electrodeless microwave energy activated curing system available as the I-600-M from Fusion Systems Corporation operating at from 400 to 600 watts/inch.

The cured composition is subject to testing for adhesivity (i.e., the bond between the scrim reinforced gel and a substrate, e.g., a standard stainless steel plate or possibly the Mylar® film web upon which the scrim reinforced gel is coated prior to being irradiated), using the Satec T1000 material Testing Machine (SATEC Systems, Grove City, Pa.) equipped with an adjustable tilt table set for 90°. The test procedure for 90° peel strength requires the pulling of a one-inch-wide strip of gel from the substrate (stainless steel plate or Mylar® web) at 12 inches/minute and at an angle of 90' to the plane of the sample as per ASTM D1876, ASTM D3330M (American Society for Testing. Materials, Philadelphia, Pa.) or PSTC-1 and -3 (Pressure Sensitive Tape Council, Glenview, Ill.), and recording the average peel force in grams/one inch-width. (ASTM D3330M and PSTC-1 and -3 are for 180° peel testing but were adapted for use in this Example.)

The formulations of Table 1 are prepared similarly, except that various different ingredients may be utilized as specifically noted in Table 1.

Certain of the ingredients (components) of the formulations of Table 1 are as follows:

| | |
|---|---|
| Irgacure ® 2959 | Photoinitiator available from Ciba Specialty Chemicals |
| SR-9035 | 15-mole ethoxylated trimethylol propane triacrylate from Sartomer |
| Actilane 755 | Amine synergists available from Akzo |
| Actilane 705 | Nobel Chemicals America |
| CN 373 | Reactive amine coinitiators available |
| CN 383 | from Sartomer |
| SR 511 | 2-Hydroxyethlethylene urea available From Sartomer |
| Hawaiian Blue | Available from Chefmaster ® |
| FA1Q8OBC | Acryloxyethyl dimethyl ammonium Chloride available from Ciba |
| Neodox ™ 25-11 | Alcohol ethyl carboxylate available From Hickson DanChem |
| ESACURE DP-250 | Photoinitiator Mixture available from Lamberti |

The compositions of the present invention are suitable for fabricating a medical electrode that accomplish the objects of this invention, i.e. the compositions of Table I are soft hydrogels, adhesive to human skin, and having the requisite flexibility and elasticity. The compositions of Table 1 are softer, low in adhesion, and leggy as compared to similar compositions without a glycol vinyl ether component.

| | | | | NOTE BOOK NUMBER | | | | | |
|---|---|---|---|---|---|---|---|---|---|
| COMPONENT | 21-59B | 23-06B | 23-26 | 23-38A | 23-43C | 23-87A | 23-88A | COMPONENT |
| D.I Water | 20.80% | 21.80% | 23.20% | 21.00% | 21.70% | 24.50% | 25.50% | D.I Water |
| Magnesium Acetate | 2.00% | | | | | | | Magnesium Acetate |
| Triethanolamine 99% | 1.10% | | | | | | | Triethanolamine 99% |
| Glycerin | 50.00% | 50.00% | 50.00% | 50.00% | 50.00% | 50.00% | 50.00% | Glycerin |
| UREA 511 | | | 2.00% | | | 3.00% | 3.00% | UREA 511 |
| PVP/VA K-90 | | | | | | | | PVP/VA K-90 |
| FA1Q80BC | | | | | | | | FA1Q80BC |
| Acrylic Acid | 16.00% | 12.00% | 12.00% | 12.00% | 12.00% | 12.00% | 12.00% | Acrylic Acid |
| *DEGMVE | 8.00% | 6.00% | 6.00% | 6.00% | 6.00% | | | *DEGMVE |
| 50% Sodium AMPS | | | | | | | | 50% Sodium AMPS |
| Potassium Chloride | | | | | | | | Potassium Chloride |
| Potassium Alum | | | | | | | | Potassium Alum |
| Sodium Hydroxide | | 3.50% | 3.00% | 3.00% | 3.00% | 3.00% | 3.00% | Sodium Hydroxide |
| K-Na Tartrate | | 1.00% | 1.00% | 1.00% | 1.00% | 1.00% | 1.00% | K-Na Tartrate |
| Hydrogen Peroxide | | 2.00% | | | | | | Hydrogen Peroxide |
| L-Arginine (pure) | | | | 4.00% | | | | L-Arginine (pure) |
| Glycine | | | | | 4.00% | | | Glycine |
| **TMVE | | | | | | 4.00% | | **TMVE |
| ***EGVE | | | | | | | 3.00% | ***EGVE |
| K2HPO4 | | | | | | | | K2HPO4 |
| NaH2PO4 | | | | | | | | NaH2PO4 |
| 50% NaOH | | | | | | | | 50% NaOH |
| Hawaiian Blue | | | | | | | | Hawaiian Blue |
| NVP | | | | | | | | NVP |
| 3% I-184 (in IPA) | 1.00% | 1.00% | 1.00% | 1.00% | 1.00% | 1.00% | 1.00% | 3% I-184 (in IPA) |
| Irgacure 2959 | | | | | | | | Irgacure 2959 |
| Tin Octoate | | | | | | | | Tin Octoate |
| SR-9035 | | | | | | | | SR-9035 |
| 1% MBA (in water) | 0.80% | 2.00% | 1.20% | 1.50% | 0.90% | 1.00% | 1.00% | 1% MBA (in water) |
| MBA | | | | | | | | MBA |
| CN-383 | 0.30% | 0.70% | 0.60% | 0.50% | 0.40% | 0.50% | 0.50% | CN-383 |
| Actilane 755 | | | | | | | | Actilane 755 |
| DP-250 | | | | | | | | DP-250 |
| Actilane 705 | | | | | | | | Actilane 705 |
| CN-373 | | | | | | | | CN-373 |
| Neodox 25-11 | | | | | | | | Neodox 25-11 |

-continued

| | 100.00% | 100.00% | 100.00% | 100.00% | 100.00% | 100.00% | 100.00% | |

| | NOTE BOOK NUMBER | | | | | | |
| --- | --- | --- | --- | --- | --- | --- | --- |
| COMPONENT | 23-88B | 28-92 | 31-81B | 41-33B | 51-10 | 51-30 | COMPONENT |
| D.I Water | 24.50% | 17.10% | 18.10% | 17.50% | 16.30% | 19.10% | D.I Water |
| Magnesium Acetate | | | | | | | Magnesium Acetate |
| Triethanolamine 99% | | | | | 7.50% | 7.70% | Triethanolamine 99% |
| Glycerin | 50.00% | 54.00% | 46.00% | 49.00% | 48.00% | 48.00% | Glycerin |
| UREA 511 | 3.00% | | 4.50% | 5.00% | 4.45% | 4.40% | UREA 511 |
| PVP/VA K-90 | | | | 2.00% | | | PVP/VA K-90 |
| FA1Q80BC | | 12.00% | | | | | FA1Q80BC |
| Acrylic Acid | 12.00% | 3.40% | 10.00% | 11.00% | 11.00% | 11.00% | Acrylic Acid |
| *DEGMVE | | 6.00% | 6.50% | 10.06% | 8.80% | 8.60% | *DEGMVE |
| 50% Sodium AMPS | | | 7.00% | | | | 50% Sodium AMPS |
| Potassium Chloride | | | | | 3.00% | | Potassium Chloride |
| Potassium Alum | | | | | | 0.20% | Potassium Alum |
| Sodium Hydroxide | 3.00% | | | | | | Sodium Hydroxide |
| K-Na Tartrate | 1.00% | | 1.00% | | | | K-Na Tartrate |
| Hydrogen Peroxide | | 2.00% | | | | | Hydrogen Peroxide |
| L-Arginine (pure) | | | | | | | L-Arginine (pure) |
| Glycine | | | | | | | Glycine |
| **TMVE | | | | | | | **TMVE |
| ***EGVE | 4.00% | | | | | | ***EGVE |
| K2HPO4 | | 1.50% | | | | | K2HPO4 |
| NaH2PO4 | | | | 0.60% | | | NaH2PO4 |
| 50% NaOH | | | 4.00% | 4.00% | | | 50% NaOH |
| Hawaiian Blue | | 0.50% | 0.50% | 0.50% | 0.50% | 0.30% | Hawaiian Blue |
| NVP | | | 2.00% | | | | NVP |
| 3% I-184 (in IPA) | 1.00% | 1.00% | | | | | 3% I-184 (in IPA) |
| Irgacure 2959 | | | 0.20% | | | | Irgacure 2959 |
| Tin Octoate | | | 0.10% | | | | Tin Octoate |
| SR-9035 | | | | 0.06% | 0.03% | 0.03% | SR-9035 |
| 1% MBA (in water) | 1.00% | 2.00% | | | | | 1% MBA (in water) |
| MBA | | | 0.10% | | | | MBA |
| CN-383 | 0.50% | 0.50% | | 0.20% | | | CN-383 |
| Actilane 755 | | | | | 0.10% | | Actilane 755 |
| DP-250 | | | | 0.08% | 0.17% | 0.17% | DP-250 |
| Actilane 705 | | | | | 0.15% | 0.15% | Actilane 705 |
| CN-373 | | | | | | 0.30% | CN-373 |
| Neodox 25-11 | | | | | | 0.05% | Neodox 25-11 |
| | 100.00% | 100.00% | 100.00% | 100.00% | 100.00% | 100.00% | |

*DEGMVE Diethyleneglycol monovinyl ether
**TMVE Tri(ethylene glycol)methyl vinyl ether
***EGVE Ethylene glycol vinyl ether As an example, composition 51-30 was evaluated in a Texture Analyzer Study as described in TA, XT 2i Texture Analyzer Study: Sealants & Caulking for Bath and Kitchen Study #I-92 available from Texture Technologies Corp. of Searsdale, N.Y., which is hereby incorporated by reference and made a part of this specification. The results are shown in FIG. 3.

The Texture Analyzer is a probe that pushes into the gel then pulls out of the gel. The graphs are plots of Force vs. time. The first peaks $A^1$, $A^2$, $A^3$, $A^4$ represent the force of resistance to compression and the areas under the peaks represent the compressive work done to penetrate 40% of the gel thickness. The second peaks $B^1$, $B^2$, $B^3$, $B^4$ under the baseline are the maximum adhesive forces and the areas under the peaks represent the adhesive work. If there are two adhesive peaks, the gel is yielding (narrowing and possibly stringing). When the gel lets go, the plots go back to baseline.

Figure 3:
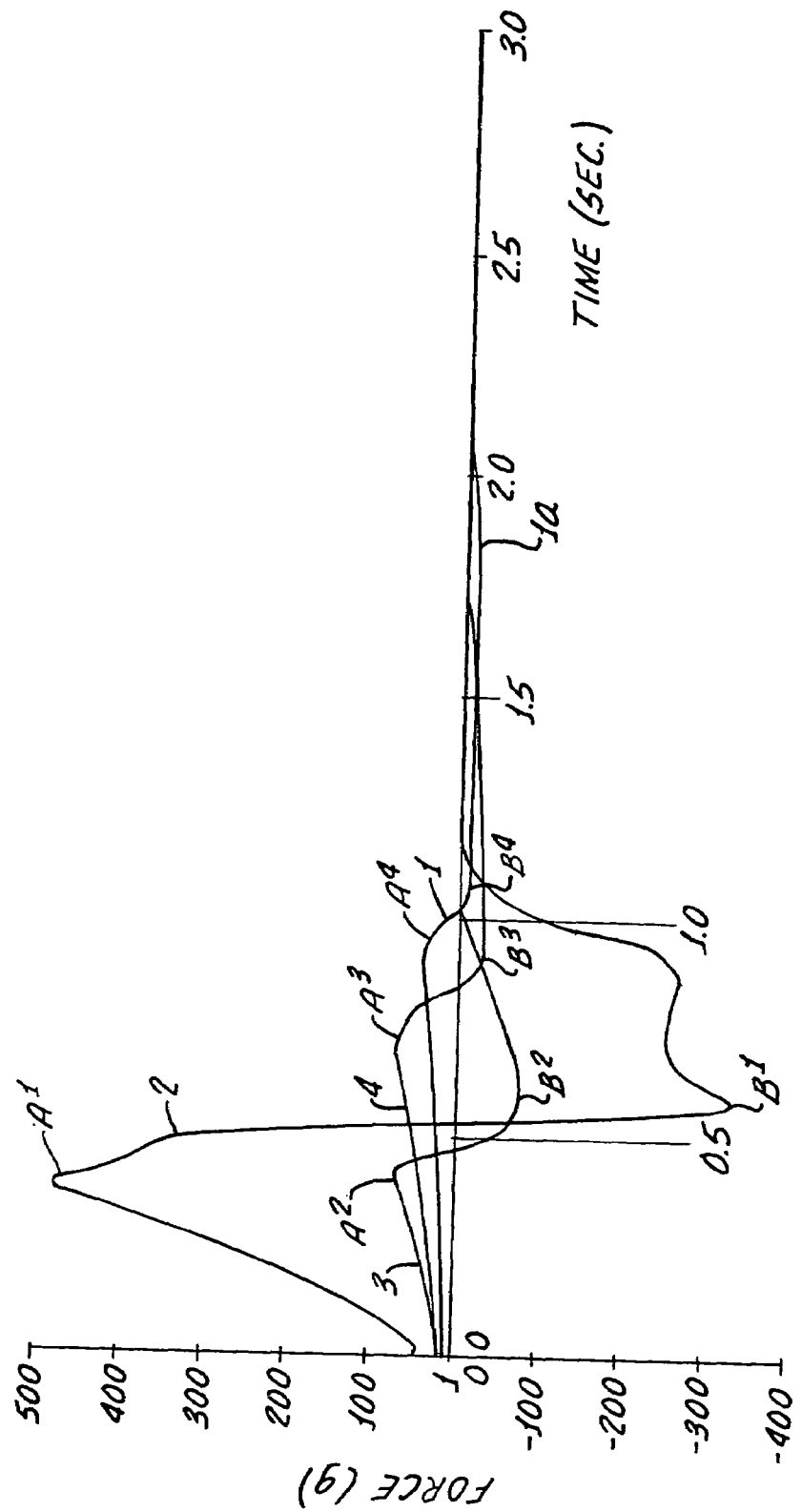
FIG. 3 is a texture analysis plot.

In FIG. 3, a composition (51-30) of this invention (plot 1) is compared to on acrylate copolymer gel comprising a sodium salt of 2-acrylamido propane sulfonic acid and sodium salt of acrylic acid (plot 2). As compared to the pure acrylate gel, the composition of this invention is softer, as shown by the smaller late peak, which is the compression force peak, lower in adhesion, as shown by the small flat peak, and leggy, as shown by the time of release i.e. it holds onto the probe the longest, see plot segment 1a. The composition of this invention rolls off the probe in a wave without yielding.

Also shown in FIG. 3 is plot 3 representing composition 51-97, (no DEGMVE) and plot 4 representing a polyvinyl pyrrolidone adhesive available from Valley Lab, Inc. As shown both plots 3 and 4 have a greater and shorter peak $A^2$, $A^3$ and peaks $B^2$, $B^3$.

EXAMPLE II

The compositions designated 23-38A in Table I, above, was tested for biocompatibility in the following tests:

An in vitro biocompatibility study, based on the United States Pharmacopeia (USP) guidelines, was conducted on a test article, i.e. Composition 23-38, to determine the potential for cytotoxicity. A 1.0 $cm^2$ portion of the test article, the negative control, and the positive control were each placed on duplicate agarose surfaces directly overlaying confluent monolayers of L-929 mouse fibroblast cells. After incubating at 37°C. in 5% $CO_2$ for 24-26 hours, the cell cultures were examined macroscopically for cell decolorization around the test article and controls to determine the zone of cell lysis (if any). The cultures were then examined microscopically (100X) to verify any decoborized zones and to determine cell morphology in proximity to and beneath the test and control articles.

Under the conditions of this study, the test article showed no evidence of causing cell lysis or toxicity. The test article met the requirements of the USP. The negative and positive controls performed as anticipated.

The test article, Composition 23-38A, was evaluated for primary skin irritation in accordance with the guidelines of the International Organization for Standardization 10993: Biological Evaluation of Medical Devices, Part 10: Tests for Irritation and Sensitization. Two 25 mm×25 mm sections of the test article and control article were topically applied to the skin of three rabbits and left in place for 24 hours. The sites were graded for erythema and edema at 1, 24, 48 and 72 hours after removal of the single sample application.

Under the conditions of this study, no irritation was observed on the skin of the rabbits. The Primary Irritation Index for the test article was calculated to be 0.0. The response of the test article was categorized as negligible.

A study was conducted in the guinea pig to evaluate the potential for delayed dermal contact sensitization of Composition 23-38A. The study was conducted based on the requirements of the International Organization for Standardization 10993: Biological Evaluation of Medical Devices, Part 10: Tests for Irritation and Sensitization.

The test article was occlusively patched for 6 to 8 hours to the intact skin of 10 guinea pigs, three times a week, for a total of nine induction treatments over a 3 week period. The control article was similarly patched to 5 guinea pigs. Following a recovery period, the 10 test and 5 control animals received a challenge patch of the test article and the control article. All sites were observed for evidence of dermal reactions at 24, 48, and 72 hours after patch removal.

Under the conditions of this study the test article showed no evidence of causing delayed dermal contact sensitization in the guinea pig.

It is well known that acrylic gels in general do not perform adequately in the above tests particularly cytotoxicity. (R. Schwalm, et. al., "Vinyl Ethers in UV Curing: Copolymers With Acrylates and Unsaturated Polyesters": Conf. Proc Rad Tech Europe 99; Berlin, Germany; Nov. 8-10, 1999, p 103-109)

The acrylic acid-glycol vinyl ether gels of the present invention achieve perfect scores in the above tests.

In human wear testing on 20 persons (10 male, 10 female) no skin reaction was noted. Three of test subjects have been sensitized to acrylic hydrogel, and experienced no skin reaction to the present invention.

In addition, the gels of present invention have no apparent drying after exposure to the atmosphere between a few days and up to about at least 3 years or longer.

It is noted that the biggest problem that had to be overcome in preparing the above Examples was vinyl ether monomer hydrolysis. There is little basic hydrolysis but there is neutral and substantial acidic hydrolysis with acidity determining the rate. This presented a major impediment when acrylic acid was utilized as a comonomer with a glycol vinyl ether since acrylic acid polymerization is more effective as the pH is lowered. (See U.S. Pat. No. 5,352,713 at column 5, lines 10 and 11, wherein it is stated that acid moieties react with vinyl ethers even in non-water containing systems such as the free radical co-polymerized acrylate-vinyl ether polymer coatings disclosed therein.) Thus, the polymerization reaction is carried out, preferably, at a pH of from about 3.5 to 5.5 to yield a gel having a pH of from about 3.8 to 6.7.

While particular embodiments of the invention have been described, it will be understood, of course, that the invention is not limited thereto since many obvious modifications can be made and it is intended to include within this invention any such modifications as will fall within the scope of the appended claims. For example, it will be appreciated, by those skilled in the art that other alkaline materials can be utilized to neutralize the acrylic acid monomer, e.g., mono and poly positive alkaline materials, e.g., sodium, potassium, calcium, magnesium, aluminum basic oxides, hydroxides or carbonates may be used as well as ammonium hydroxide, etc.

Other thickeners or viscosity increasing agents which may be used in the medical electrodes of the present invention include polyacrylamide, polyvinyl alcohol, polyacrylic acid, polyethylene oxide, methyl cellulose, ethyl cellulose, carboxymethyl cellulose, hydroxyethyl cellulose and polyacrylamide-alkylsulfonic acid.

Finally, the conductive polymer may include particulate reinforcing agents and/or fillers, such as silica, e.g. Cabosil®.

What is claimed is:

1. A conductive organic polymer comprising an electrically conductive organic polymer plasticized with a polyhydric alcohol with organic polymer being from a monomeric mixture comprising from about 2 to 30 pph acrylic acid, 2 to 30 pph of a glycolvinylether, and 0.01 to 1.5 pph of a crosslinking agent.

2. The polymer of claim 1 wherein polyhydric alcohol is glycerol.

3. The polymer of claim 2 wherein crosslinking agent is selected from the group consisting of methylene bis-acrylamide and polyethylene glycol diacrylates and dimethacrylates having a molecular weight from about 200 to about 600, and ethoxylated trimethylolpropane triacrylate (ETMPTA).

4. The polymer of claim 3 wherein crosslinking agent is ETMPTA.

5. The polymer of claim 1 wherein glycolvinylether is selected from the group consisting of hydroxybutylvinylether, ethyleneglycolvinylether, diethylene glycol vinylether, and triethyleneglycolmethylvinylether.

6. The polymer of claim 5 wherein glycol-vinylether is diethylene glycol vinyl ether.

7. The polymer of claim 5 wherein monomeric mixture further comprises from about 35 to 60 pph of glycerol.

8. The polymer of claim 7 wherein at least a portion of acrylic acid is replaced with 2-acrylamido propane sulfonic acid (AMPS) or a cationic acrylic ester.

9. The polymer of claim 1 wherein monomeric mixture further comprises from 0.01 to 3 pph of ultraviolet sensitive curing agents.

10. The polymer of claim 9 wherein ultraviolet sensitive curing agent is selected from the group consisting of 2-hydroxy-2-methyl-1-phenylpropan-2-one, 4-(2-hydroxyethoxy)phenyl (2-hydroxy-2-phenyl-2-hydroxy-2-propyl) ketone, 2,2-dimethoxy-2-phenyl-acetophenone 1-[4-(2-Hydroxyethoxy)-phenyl]2hydroxy2-methyl-1-propane-1-one, 1-hydroxycyclohexylphenyl ketone, trimethyl benzoyl diphenyl phosphine oxide and mixtures thereof.

11. The polymer of claim 10 wherein mixture comprises from 5 to 25 pph acrylic acid and from 5 to 25 pph of a glycolvinylether.

12. The polymer of claim 11 wherein glycolvinylether is selected from the group consisting of hydroxybutylvinylether, ethyleneglycolvinylether, diethylene glycol vinylether, and triethyleneglycolmethylvinylether.

13. The polymer of claim 12 wherein glycol vinylether is diethylene glycol vinyl ether.

14. The polymer of claim 11 wherein monomeric mixture further comprises an aldehyde reactant or neutralizer.

15. The polymer of claim 14 wherein aldehyde reactant or neutralizer is selected from the group consisting of hydrogen peroxide, hydroxyethylethylene urea and L-arginine hydrochloride.

16. The polymer of claim 15 wherein aldehyde reactant or neutralizer is 2-hydroxyethylethylene urea.

* * * * *